(12) United States Patent
Kirschner

(10) Patent No.: US 8,791,078 B2
(45) Date of Patent: *Jul. 29, 2014

(54) CELL PROTECTION IN DIALYSIS PATIENTS BY ADMINISTRATION OF A CREATINE COMPOUND

(75) Inventors: Ulrich Kirschner, Cologne (DE); Jan Bulle, legal representative, Cologne (DE)

(73) Assignee: Crearene Ltd., Nassau (BS)

( * ) Notice: Subject to any disclaimer, the term of this patent is extended or adjusted under 35 U.S.C. 154(b) by 0 days.

This patent is subject to a terminal disclaimer.

(21) Appl. No.: 13/386,310

(22) PCT Filed: Jul. 21, 2010

(86) PCT No.: PCT/EP2010/004458
§ 371 (c)(1),
(2), (4) Date: Feb. 13, 2012

(87) PCT Pub. No.: WO2011/009601
PCT Pub. Date: Jan. 27, 2011

(65) Prior Publication Data
US 2012/0135943 A1     May 31, 2012

(30) Foreign Application Priority Data
Jul. 24, 2009 (EP) .................... 09009618

(51) Int. Cl.
| | | |
|---|---|---|
| *A61K 31/7004* | (2006.01) | |
| *A61P 7/08* | (2006.01) | |
| *B65D 25/08* | (2006.01) | |
| *A61K 31/19* | (2006.01) | |
| *A61K 45/06* | (2006.01) | |
| *A61K 33/10* | (2006.01) | |
| *A61K 33/06* | (2006.01) | |

(52) U.S. Cl.
CPC .............. *A61K 31/19* (2013.01); *A61K 45/06* (2013.01); *A61K 33/10* (2013.01); *A61K 33/06* (2013.01)
USPC .............................. 514/23; 514/565; 206/219

(58) Field of Classification Search
CPC ....... A61K 31/19; A61K 45/06; A61K 33/10; A61K 33/06
USPC ..................... 514/23, 565; 206/219
See application file for complete search history.

(56) References Cited

U.S. PATENT DOCUMENTS

| | | | | |
|---|---|---|---|---|
| 4,959,175 A | * | 9/1990 | Yatzidis ................. | 252/364 |
| 2003/0013767 A1 | | 1/2003 | Bessman | |
| 2006/0226080 A1 | * | 10/2006 | Degreve et al. ............ | 210/647 |
| 2012/0101069 A1 | * | 4/2012 | Moeddel et al. ........... | 514/115 |

FOREIGN PATENT DOCUMENTS

WO    2010/115291 A1    10/2010

OTHER PUBLICATIONS

Chang, Chiz-Tzung et al.; "Creatine monohydrate treatment alleviates muscle cramps associated with haemodialysis"; Nephrology Dialysis Transplantation; vol. 17, No. 11; Nov. 2002; pp. 1978-1981; XP002546996.

Taes, Youri E. et al.; "Guanidino compounds after creatine supplementation in renal failure patients and their relation to inflammatory status"; Nephrology Dialysis Transplantation; vol. 23, No. 4; Apr. 2008; pp. 1330-1335; XP002546997.

Taes, Youri E. et al.; "Creatine supplementation does not decrease total plasma homocysteine in chronic hemodialysis patients"; Kidney International; vol. 66, No. 6; Dec. 2004; pp. 2422-2428; XP002546998.

* cited by examiner

*Primary Examiner* — Brandon Fetterolf
*Assistant Examiner* — Yin-Horng Shiao
(74) *Attorney, Agent, or Firm* — Rankin, Hill & Clark LLP

(57) ABSTRACT

The invention relates to a dialysis solution for haemodialysis or peritoneal dialysis, said solution having a theoretical osmolarity within the range of from 250 to 550 mosm/L and a pH value within the range of from 4.9 to 8.0, said solution comprising a creatine compound and one or more electrolytes, wherein the concentration of the creatine compound is not more than 50 mM.

20 Claims, No Drawings

CELL PROTECTION IN DIALYSIS PATIENTS BY ADMINISTRATION OF A CREATINE COMPOUND

FIELD OF THE INVENTION

The invention generally relates to cell protection in dialysis patients by administration of dialysis fluids containing suitable amounts of a creatine compound, and in particular to the use of a creatine compound to counteract pathophysiological states that occur in dialysis patients in the course of conventional haemodialysis or peritoneal dialysis.

BACKGROUND ART

Creatine is a nitrogenous organic acid that occurs naturally in vertebrates and helps to supply energy to muscle. In humans, about half of the daily creatine is biosynthesized from three different amino acids- arginine, glycine, and methionine. The rest is taken in by alimentary sources.

Cells take up creatine that is subsequently phosphorylated by intra-cellular creatine kinase to give high-energy-rich phospho-creatine (PCr). By elevation of intra-cellular phospho-creatine levels, creatine supplementation improves the cellular energy status, i.e. by increasing the PCr/ATP energy-charge ratio and intracellular energy trafficking via the PCr/Cr shuttle. Creatine stimulates mitochondrial respiration and thus improves energy production in mitochondria. Creatine also activates the AMP-stimulated protein kinase (AMPK) a general energy sensor and cell stress kinase that improves energy provision via enhancing glucose uptake and oxidation in cells.

During the dialysis process, blood cells are subjected to metabolic, mechanical, osmotic, oxidative and other stresses, which can lead to loss of cell function and cell death. Anemia, reduced immune response, osteoporosis, osteomalacia, adynamic bone disease, cognitive dysfunctions are among the most common adverse events encountered in dialysis patients.

C.-T. Chang et al., Nephrol Dial Transplant 2002, 17, 1978-81 disclose that oral creatine monohydrate treatment alleviates muscle cramps associated with haemodialysis. 12 mg of creatine monohydrate was given to each patient before each dialysis session for 4 weeks.

Y. E. C. Taes et al., Kidney International 2004, 66, 2422-8 disclose that oral creatine supplementation does not decrease total plasma homocysteine in chronic haemodialysis patients. Patients were treated orally with creatine (2 g/day).

Y. E. C. Taes et al., Nephrol Dial Transplant 2008, 23, 1330-5 investigate guanidino compounds after exogenous creatine supplementation in renal failure patients and their relation to inflammatory status. Patients received 2 g creatine orally and daily.

It is an object of the invention to provide dialysis solutions that have advantages compared to the dialysis solutions of the prior art.

This object is solved by the subject-matter of the patent claims.

SUMMARY OF THE INVENTION

The invention relates to a dialysis solution for haemodialysis or peritoneal dialysis, said solution having a theoretical osmolarity within the range of from 250 to 550 mosm/L and a pH value within the range of from 4.9 to 8.0, said solution comprising a creatine compound and one or more electrolytes, wherein the concentration of the creatine compound is not more than 50 mM.

It has been surprisingly found that supplementation of dialysis fluid by a creatine compound in comparative low concentrations leads to significant cell protection and thus to a health benefit for haemodialysis patients.

DETAILED DESCRIPTION OF THE INVENTION

A first aspect of the invention relates to a dialysis solution for haemodialysis or peritoneal dialysis, said solution having a theoretical osmolarity within the range of from 250 to 550 mosm/L and a pH value within the range of from 4.9 to 8.0, said solution comprising a creatine compound and one or more electrolytes, wherein the concentration of the creatine compound is not more than 50 mM.

Dialysis preparations are commercialized in various forms. Typically, dialysis preparations are commercialized as concentrates, as multi-component systems or as ready-to-use dialysis fluids.

For the purpose of the specification, the term "dialysis solution" refers to a ready-to-use dialysis fluid, i.e. to a liquid preparation which is adapted to being administered to the patient as such. In particular, the dialysis solution does not require any dilution steps, mixing steps with other compositions, and the like.

In contrast to such dialysis solutions, concentrates, either liquid or solid, need to be diluted with or dissolved in water and aqueous fluids, respectively, prior to administration. Similarly, multi-component systems need to be mixed with one another prior to administration. Concentrates and multi-component systems have in common that they can be regarded as precursors of the dialysis solution according to the invention.

The dialysis solution according to the invention is either for haemodialysis or for peritoneal dialysis. Dialysis solutions for haemodialysis or for peritoneal dialysis usually contain electrolytes with a concentration close to the electrolytic composition of plasma. Electrolytes typically include sodium or potassium, calcium, magnesium and chloride ions.

Dialysis solutions must have a physiologically acceptable pH value. This is typically achieved by the presence of buffers (buffer systems) which in turn may also contribute to the overall content of electrolytes. Typical buffers include bicarbonate, lactate and pyruvate.

Further, dialysis solutions must have a physiologically acceptable osmolarity. This is typically achieved by the electrolytes and other osmotic agents, typically non-ionic tonicity agents such as glucose, which is tolerated well in the desired osmolarity range.

The dialysis solution according to the invention has a theoretical osmolarity within the range of from 250 to 550 mosm/L. The skilled person knows how to determine the theoretical osmolarity. Typically, it is calculated on the basis of the individual amounts of all ingredients.

Preferably, particularly when the dialysis solution is for haemodialysis, the theoretical osmolarity is within the range of from 250 to 335 mosm/L, more preferably 260 to 325 mosm/L, still more preferably 270 to 315 mosm/L, yet more preferably 275 to 310 mosm/L, most preferably 280 to 305 mosm/L and in particular 285 to 300 mosm/L.

Preferably, particularly when the dialysis solution is for peritoneal dialysis, the theoretical osmolarity is within the range of from 300 to 565 mosm/L, more preferably 310 to 555 mosm/L, still more preferably 320 to 545 mosm/L, yet more preferably 330 to 535 mosm/L, most preferably 340 to 525 mosm/L and in particular 350 to 515 mosm/L. In a preferred embodiment, the theoretical osmolarity is within the range of 355±55 mosm/L, more preferably 355±45 mosm/L, still more preferably 355±35 mosm/L, yet more preferably 355±25 mosm/L, most preferably 355±15 mosm/L and in particular 355±10 mosm/L. In another preferred embodiment, the theoretical osmolarity is within the range of 400±55 mosm/L, more preferably 400±45 mosm/L, still more preferably 400±35 mosm/L, yet more preferably 400±25 mosm/L, most preferably 400±15 mosm/L and in particular 400±10 mosm/L. In still another preferred embodiment, the theoretical osmolarity is within the range of 510±55 mosm/L, more preferably 510±45 mosm/L, still more preferably 510±35 mosm/L, yet more preferably 510±25 mosm/L, most preferably 510±15 mosm/L and in particular 510±10 mosm/L.

The dialysis solution according to the invention has a pH value within the range of from 4.9 to 8.0, more preferably 5.2 to 7.8, preferably under ambient conditions. In a preferred embodiment, the pH value is within the range of 5.5±0.6, more preferably 5.5±0.5, still more preferably 5.5±0.4, yet more preferably 5.5±0.3, most preferably 5.5±0.2 and in particular 5.5±0.1. In another preferred embodiment, the pH value is within the range of 7.0±0.6, more preferably 7.0±0.5, still more preferably 7.0±0.4, yet more preferably 7.0±0.3, most preferably 7.0±0.2 and in particular 7.0±0.1. In still another preferred embodiment, the pH value is within the range of 7.4±0.6, more preferably 7.4±0.5, still more preferably 7.4±0.4, yet more preferably 7.4±0.3, most preferably 7.4±0.2 and in particular 7.4±0.1.

The dialysis solution according to the invention comprises a creatine compound. For the purpose of the specification, the term "creatine compound" encompasses creatine ($H_2NC(=NH)N(CH_3)CH_2CO_2H$), physiologically acceptable creatine precursors, analogues or produgs, and physiologically acceptable salts of any of the foregoing, In particular, a creatine compound can be creatine monohydrate, creatine phosphate, the creatine analog cyclocreatine, the creatine precursor guanidoacetic acid, and hydrosoluble organic salts of creatine. Preferably, the creatine compound is selected from the group consisting of creatine and physiologically acceptable salts thereof, preferably creatine monohydrate.

The dialysis solution according to the invention comprises the creatine compound at a concentration of not more than 50 mM. Preferably, the dialysis solution comprises the creatine compound at a concentration of not more than 40 mM, more preferably not more than 30 mM, still more preferably not more than 20 mM, yet more preferably not more than 10 mM, most preferably not more than 5.0 mM and in particular not more than 2.5 mM.

In a preferred embodiment, the concentration of the creatine compound is within the range of from 0.001 to 2.5 mM, from 0.004 to 1.2 mM, or from 0.8 to 1.2 mM.

US 2003 0013767 A1 discloses a method of using a creatine compound to treat muscle loss associated with liver and kidney diseases. Creatine monohydrate is administered by dialysis. The dialysis fluids contain creatine monohydrate in concentrations of up to about 1.5 g/100 mL of fluid. These concentrations of creatine, however, are highly nonphysiological and likely to exert a high-osmotic pressure and metabolic stress on cells and thus, may cause damage to cells and even be toxic. In addition, as an unfavorable and undesired side effect, exposure of the organism to high concentrations of creatine reduces endogenous creatine synthesis in the body. Further, the high concentrations of creatine proposed in US 2003/0013767 A1 are technically impractical, due the rather low solubility of creatine in water and the very large temperature-dependence of the creatine solubility. It is a high risk that under the high-concentration conditions of up to 15 g of creatine per liter of fluid, which is at the solubility limit of a creatine solution at 25° C., creatine will precipitate in the dialysis fluid with all of the very unfavorable consequences for the practicability of the dialysis process.

The concentrations of creatine in the dialysis solution according to the invention (final dialysis liquid), however, are lower by a factor of 100× compared to those proposed by US 2003/0013767 A1, but are effective for cell protection. During the dialysis process, the patient is exposed to the total amount of creatine that has been added to the concentrated dialysis fluid. These concentrations of creatine are absolutely physiological, e.g. such concentrations of creatine appear post-prandial in the serum of a human after a good meal of meat of fish or after a single dose of creatine supplementation with 5-20 g of creatine orally. Such creatine concentrations, as proposed herein, do not have any side effects and will not lead to any down-regulation of endogenous creatine synthesis in the body.

It has been surprisingly found that the general protection of cells in the body by creatine compounds is especially relevant for erythrocytes and white blood cells that are oxidatively stressed during the process of haemodialysis. There is evidence that creatine compounds reduce anemia and weakening of the immune response that are commonly observed in haemodialysis patients. Creatine compounds appear to enhance the levels of carnosin and anserin in muscle, compounds that are involved in reducing Advanced Protein Glycation (AGE) that is inflicted in faster cell aging. Thus, supplementation by creatine compounds leads to cell protection and acts as anti-aging intervention also for haemodialysis patients.

Further, creatine supplementation has been shown to reduce serum levels of homocysteine, a significant cardiovascular risk factor that is also generally elevated in haemodialysis patients. Thus, haemodialysis patients take profit from supplementation of a creatine compound by reducing homocysteine concentration in their blood and lower the risk of cardiovascular damage.

Still further, creatine acts as a pleiotropic nutritional supplement. Therefore, it is likely that there are many more positive effects of creatine compounds on cells and tissues dialysis patients profit from.

The dialysis solution according to the invention comprises one or more electrolytes.

In general, an electrolyte is any substance containing free ions that behaves as an electrically conductive medium. Preferably, the electrolytes completely dissociate into cations and anions without substantially changing the pH value of the aqueous composition. In this regard, electrolytes can be distinguished from buffers. Preferably, all electrolytes are present in concentrations which ensure complete dissolution in water.

Preferred cations are selected from alkaline metals such as $Na^+$ and $K^+$ and alkaline earth metals such as $Ca^{2+}$ and $Mg^{2+}$. A preferred anion is Cr.

The dialysis solution according to the invention may contain further anions such as hydrogen carbonate (bicarbonate), acetate, lactate, pyruvate and the like, but for the purpose of the specification, due to their basicity, such anions in combination with suitable cations are preferably not considered as electrolytes but as buffers.

In a preferred embodiment, the dialysis solution according to the invention contains $Na^+$ ions. Preferably, the concentration of the $Na^+$ ions is within the range of from 100 to 180 mM, more preferably from 110 to 170 mM, still more preferably from 115 to 165 mM, yet more preferably from 120 to 160 mM, most preferably from 125 to 155 mM and in particular from 130 to 150 mM. In another preferred embodiment, however, the dialysis solution according to the invention does not contain $Na^+$ ions.

In a preferred embodiment, the dialysis solution according to the invention contains $K^+$ ions. Preferably, the concentration of the $K^+$ ions is within the range of from 0.5 to 5.0 mM, more preferably 1.0±0.75, 2.0±0.75, 3.0±0.75 or 4.0±0.75, still more preferably 1.0±0.5, 2.0±0.5, 3.0±0.5 or 4.0±0.5, and most preferably 1.0±0.25, 2.0±0.25, 3.0±0.25 or 4.0±0.25. In another preferred embodiment; however, the dialysis solution according to the invention does not contain $K^+$ ions.

In a preferred embodiment, the dialysis solution according to the invention contains $Ca^{2+}$ ions. Preferably, the concentration of the $Ca^{2+}$ ions is within the range of from 0.5 to 2.0 mM, more preferably 1.0±0.75, 1.25±0.75, 1.5±0.75 or 1.75±0.75, still more preferably 1.0±0.5, 1.25±0.5, 1.5±0.5 or 1.75±0.5, and most preferably 1.0±0.25, 1.25±0.25, 1.5±0.25 or 1.75±0.25. In another preferred embodiment, however, the dialysis solution according to the invention does not contain $Ca^{2+}$ ions.

In a preferred embodiment, the dialysis solution according to the invention contains $Mg^{2+}$ ions. Preferably, the concentration of the $Mg^2$ ions is within the range of from 0.25 to 1.50 mM, more preferably 0.75±0.75 or 1.0±0.75, still more preferably 0.5±0.5, 0.75±0.5 or 1.0±0.5, and most preferably 0.5±0.25, 0.75±0.25 or 1.0±0.25. In another preferred embodiment, however, the dialysis solution according to the invention does not contain $Mg^{2+}$ ions.

In a preferred embodiment, the dialysis solution according to the invention contains ions. Preferably, the concentration of the Cr ions is within the range of from 75 to 130 mM, more preferably from 80 to 125 mM, still more preferably from 85 to 120 mM, yet more preferably from 90 to 115 mM, most preferably from 95 to 120 mM and in particular from 100 to 115 mM. In another preferred embodiment, however, the dialysis solution according to the invention does not contain $Cl^-$ ions.

Preferably, the dialysis solution according to the invention additionally comprises
one or more non-ionic tonicity agents (osmotics, osmotically active agents), and/or
one or more buffers.

Suitable tonicity agents are known to the skilled person. Theoretically, every compound contributes to the overall osmotic situation. For the purpose of the specification, however, tonicity agents are preferably non-ionic compounds which can be regarded neither as buffers nor as electrolytes. Typical examples of tonicity agents include glucose, glucose polymers and glycerin (glycerol).

Often glucose is used as an osmotic essentially serving to decrease the water content of the blood in an osmotically active concentration, since it has a good osmolarity and is tolerated well. A further advantage of the use of glucose is the cost advantage compared to other possible osmotics. It is also known to use glucose polymers as a substitute for or in addition to glucose. Glucose polymers are used especially for long dwelling times in peritoneal dialysis solutions due to their advantageous ultrafiltration profile. Due to the slow diffusion of glucose polymers relative to glucose, the osmolarity is essentially maintained throughout the treatment. Furthermore, the glucose load of the patient is reduced which is especially advantageous in case of diabetic patients.

In a preferred embodiment the dialysis solution according to the invention contains glucose. Preferably, the concentration of the glucose is within the range of from 1.0 to 250 mM, more preferably 5.0±4.0, 85±75, 125±75 or 235±75, still more preferably 5.0±2.5, 85±50, 125±50 or 235±50, and most preferably 5.0±1.0, 85±25, 125±25 or 235±25. In another preferred embodiment, however, the dialysis solution according to the invention does not contain glucose.

Suitable buffers are also known to the skilled person. Typical buffers include lactate salts, hydrogen carbonate salts, pyruvate salts, citrate salts, isocitrate salts, succinate salts, fumarate salts and acetate salts. A skilled person recognizes that the corresponding cation of e.g. $HCO_3^-$, e.g. $Na^+$, is a constituent of the buffer when $NaHCO_3$ is added in order to adjust the pH value, Nonetheless, as the salt dissociates in water, it also has the effect of an electrolyte. For the purpose of the specification, the preferred concentrations for the individual cations and anions shall encompass the total amount of ions, irrespective of whether they are introduced by means of electrolytes or buffers or other ingredients, such as salts of the creatine compound.

In a preferred embodiment of the present invention, the buffer contains bicarbonate. This is a very tolerable buffer system being in equilibrium with carbonate in the alkaline range and with $CO_2$ in the acidic range. Apart from or in addition to bicarbonate, other buffer systems are conceivable as well, that buffer in a physiological pH of approx. 7. Hereby, preferably substances are to be named which may be degraded easily to bicarbonate in the body. For example, lactate or pyruvate may be considered.

In a further preferred embodiment of the present invention it is envisioned that he buffer contains the salt of a weak acid, preferably lactate. The pKa of the weak acid may be <5. It may be envisioned that the buffer contains a mixture e.g. of bicarbonate and the salt of a weak acid, e.g. lactate. If the bicarbonate content is kept low, it has the advantage that the $CO_2$ pressure within the storage packaging is low. A conventional polyolefin foil may be used as a $CO_2$ barrier.

In a preferred embodiment, the dialysis solution according to the invention contains (i.e. is buffered by) $HCO_3^-$ ions. Preferably, the concentration of the $HCO_3^-$ ions is within the range of from 20 to 50 mM, more preferably from 25 to 45 mM, still more preferably from 30 to 40 mM. In another preferred embodiment, however, the dialysis solution according to the invention does not contain $HCO_3^-$ ions.

In a preferred embodiment, the dialysis solution according to the invention contains (i.e. is buffered by) lactate. Preferably, the concentration of the lactate is within the range of from 20 to 50 mM, more preferably from 25 to 45 mM, still more preferably from 30 to 40 mM. In another preferred embodiment, however, the dialysis solution according to the invention does not contain lactate.

In a preferred embodiment, the dialysis solution according to the invention contains (i.e. is buffered by) acetate. Preferably, the concentration of the acetate is within the range of from 2.0 to 7.5 mM, more preferably from 2.5 to 7.0 mM. In another preferred embodiment, however, the dialysis solution according to the invention does not contain acetate.

The total volume of the dialysis solution according to the invention is not particularly limited. Typical volumes range from several liters (suitable dosage volume for one individual) to several hundred liters (suitable stock dosage for more than one individual).

As already mentioned above, the dialysis solution according to the invention is to be considered ready-to-use, i.e. can be administered directly to a subject in need thereof, either for haemodialysis or for peritoneal dialysis.

In a preferred embodiment, the dialysis solution is a peritoneal dialysis solution that will be described in further detail hereinafter.

The peritoneal dialysis solution is biochemically balanced to correct metabolic acidosis that is associated with chronic renal failure. The peritoneal dialysis solution contains bicarbonate at a more physiological level, e.g., at a level substantially equivalent to that found in the blood that is involved in diffusive transport of solutes with dialysis fluid. In a preferred embodiment, it includes bicarbonate present at a level of approximately 20 mM/L to about 30 mM/L. In a preferred embodiment, bicarbonate is present at a level of 25 mM/L.

Additionally, the peritoneal dialysis solution preferably contains carbon dioxide at a partial pressure that is less than 60 mmHg. In a preferred embodiment the $pCO_2$ of the solution is similar to the partial pressure of carbon dioxide found in blood capillaries.

Further, preferably, the peritoneal dialysis solution has a pH value of about 7.4. Therefore, the peritoneal dialysis solution, although balanced biochemically, is a physiologically acceptable solution.

Additionally, the peritoneal dialysis solution preferably includes a weak acid with a pKa of less than 5. These weak acids are chosen so as to be normal biochemical intermediates of glucose metabolism. Preferably, the weak acids are chosen from the group consisting of: lactate; pyruvate; citrate; isocitrate; cis-aconitase; [alpha]-ketoglutarate; succinate; fumarate; malate; and oxaloacetate. These acids can be present either alone or in combination in the peritoneal dialysis solution. Preferably, the weak acids are present at a level of approximately 10 to about 20 ma/L, Preferably, the weak acid are present mainly as sodium salts. The weak acid is present in an amount that would offset the daily metabolic hydrogen production of approximately 1 mEq/kg/day.

Any tonicity agent (osmotic agent) can be used in the peritoneal dialysis solution. For example, glucose (dextrose), maltodextran, glycerol, polyglucose, polypeptides and amino acids can be used as the osmotic agent.

The peritoneal dialysis solution of the present invention balances bicarbonate at normal concentrations and has a $pCO_2$ at normal partial pressure. The weak acid under usual circumstances will have an infinite gradient from dialysate to blood. Thus, the weak acid can be expected to perform in a relatively predictable manner in correcting the metabolic acidosis of chronic uremia.

Another aspect of the invention relates to component compositions that are intended to yield the above dialysis solution according to the invention after processing according to a well defined, prescribed manner, i.e. typically following a particular protocol. Said processing may be achieved manually, i.e., by mixing separate component compositions with one another or diluting a component composition with purified water. Alternatively, however, said processing may be achieved automatically, e.g. by means of apparatuses that are intended and commercially available for that purpose. In a preferred embodiment, said processing does not lead to a dialysis solution having a static composition but rather to dialysis solution that continuously changes its composition in a dynamic fashion that is monitored by such apparatus.

For example, the creatine compound may be contained in a dialysis stock solution that is continuously diluted during the course of dialysis, such that the patient is constantly exposed to a physiological concentration of creatine during the entire dialysis treatment process. This concentration of creatine (in the final dialysis solution) is preferably in the range of 0.05 to 10 mM. This concentration is sufficient to provide those cell protection effects and health benefits for the patient.

The present invention also relates to a kit configured for the preparation of a dialysis solution according to the invention as described above, said kit comprising a first component composition,
a second component composition and
optionally, one or more further component compositions, wherein the first component composition, the second component composition and the optionally present further component composition(s) are adapted to yield the dialysis solution according to the invention when being mixed with one another.

The kit comprises at least a first component composition and a second component composition. The kit may comprise further component compositions, e.g. a third component composition and a fourth component composition. Preferably, however, the kit consists of two component compositions that preferably differ from one another.

The first component composition and the second composition can be independently of one another solid or liquid. When the component compositions are liquid, they can be selected from solutions and dispersions. Dispersions can be selected from suspensions and emulsions.

In a preferred embodiment, the first component composition is liquid, preferably pure water or an aqueous solution, and the second component composition is also liquid. In another preferred embodiment, the first component composition is liquid, preferably pure water or an aqueous solution, and the second component composition is solid, preferably a powdery mixture.

Preferably, the first component composition is a solution that may contain a tonicity agent (osmotic), calcium ions, magnesium ions, sodium ions, $H^+$ excess ions and chloride ions.

Preferably, however, the first component composition does not contain the creatine compound.

The kit according to the present invention may be provided in various forms. For example, the individual component compositions may be provided in form of separate packages, Preferably, however, the kit according to the invention is provided in form of a single packaging, such as a multichamber bag system.

Preferably, the kit according to the invention is a multichamber bag system containing the first component composition, the second component composition and the optionally present further component composition(s) in chambers separated from one another by breakable connecting arrangement(s), where the first component composition, the second component composition and the optionally present further component composition(s) can be mixed, following the breaking of the breakable connecting arrangement(s), thereby yielding the dialysis solution according to the invention.

The multichambered bag may be designed as a plastic bag having one chamber for each of the individual solutions. All the individual solutions are in separate compartments which can form a connection to one another or their outlets may open into a common line or mixing chamber. A resealable flow control element is preferably provided in this connection/outlet line, so the amount of individual solutions can be adjusted and varied individually during use. A flow control element may be, for example, a roll clamp or an occluding pump, Preferably, the multichambered bag is a twin-chambered pouch comprising a plastic pouch with at least one first chamber and one second chamber, the first component composition being included in the first chamber and the second component composition being included in the second chamber. Favorably, means are envisioned by which the two chambers are separated from each other and the activation of which enables the mixing of the content of both chambers. Hereby, the first and second chamber may be arranged adjacently. Preferably, a weld is provided which separates the chambers and opens in case of pressing onto one of the chambers, If dimensioned accordingly, the weld opens in case of pressing onto one of the fluid-filled chambers so that the contents of both chambers may be mixed and the mixture be finally administered to the patient.

In a preferred embodiment of the kit according to the invention, the first component composition is a sterilized solution containing a non-ionic tonicity agent and an acid and having a pH value below 6.0; wherein the second component composition is a sterilized solution containing a buffer and having a pH value above 7.0; wherein the first component composition and/or the second component composition and/or the optionally present further component composition(s) contain one or more electrolytes; and wherein the first component composition and/or the second component composition and/or the optionally present further component composition(s) contain the creatine compound.

The creatine compound according to the invention may be contained in portions in each of the component compositions. Preferably, however, the second component composition contains the total amount of the creatine compound.

A skilled person recognizes that combining of the individual component compositions will typically result in a diluting effect, provided that all component compositions do not already contain all ingredients in same concentrations already. For example, if the creatine compound is exclusively contained in one component composition, the combination of said component composition with another component composition will increase the overall volume of the combined composition thereby diluting, i.e. decreasing the concentration of the creatine compound. Thus, the component composition typically contains the creatine compound in a higher concentration than the final dialysis solution.

Preferably, the concentration of the creatine compound in the component composition is close to the saturation limit at 5° C. to ensure sufficient storage stability of the solution at various temperatures. In a preferred embodiment, the concentration is within the range of 6.0±1.0 g creatine compound pro liter component composition, more preferably 6.0±0.5 g.

In a preferred embodiment the second component composition comprises the total amount of the creatine compound and a suitable buffer keeping the pH value of the second component composition above 7.0, more preferably above 7.5, still more preferably above 8.0, yet more preferably above 8.5, most preferably above 9.0 and in particular above 9.5. This may be preferably achieved by $HCO_{3+}$ ions that may be present in form of e.g. dissociated $NaHCO_3$ and/or $KHCO_3$. In a preferred variant of this embodiment, the second component composition is solid and comprises a powdery mixture of the creatine compound and a suitable buffer, e.g. $NaHCO_3$ and/or $KHCO_3$.

It has been surprisingly found that the storage stability of the creatine compound can be increased by providing the creatine compound in a component composition having a comparatively high pH value. As this pH value as such might not be physiologically tolerable, the kit according to the invention comprises another component composition having a comparatively low pH value, such that when combining both component compositions prior to administration a physiologically tolerable pH value is achieved.

Preferably, the multichambered bag according to the invention is adapted for the preparation of a dialysis solution which can be used for peritoneal dialysis and which—in addition to the creatine compound—has the following compositional ranges in mval/L:

$Ca^{2+}$: 0.5-5
$Mg^{2+}$: 0-3
$Cl^-$: 90.5-121
$Na^+$: 128-145
$K^+$: 0-4
$HCO_3^-$: 25-40 in which one chamber of the bag system holds an acid concentrate containing, at least, calcium ions, and the other chamber holds a basic second concentrate, free from calcium ions and containing, at least, bicarbonate ions, where physiologically compatible acid is added to the basic concentrate, and where the two concentrates can be mixed together, following the breaking of the breakable connecting arrangement, with the formation of the dialysis solution, wherein the physiologically compatible acid is added to the basic concentrate in an amount such that the pH value is below 7.6 at room temperature.

Preferably, the physiologically compatible acid is added to the basic concentrate in an amount such that the pH value is in the range of 7,2 to 7.4.

Preferably, the basic concentrate contains sodium bicarbonate in an amount such that the hydrogen carbonate content of the finished dialysis fluid is at least 20 mmol/L.

Preferably, the hydrogen carbonate content of the basic concentrate is so great that the finished dialysis solution has between 25 and 40 mmol/L of bicarbonate ions.

Preferably, the pH value of the basic concentrate has been adjusted using HCl.

Preferably, the two concentrates are mixed with each other in a ratio of 3:1 to 1:3, and in particular of approximately 1:1.

The present invention also concerns a method of preparing a dialysis solution according to the present invention, where the desired mixing ratio is established automatically by the dialysis machine or the peritoneal dialysis cycler.

In a preferred embodiment, the invention relates to a solid preparation adapted for the preparation of a dialysis solution according to the invention when being dissolved in a predefined volume of liquid. Preferably, said preparation is a component composition as defined above and thus, a constituent of the kit according to the invention.

Preferably, the solid preparation according to the invention contains a bicarbonate salt such as $NaHCO_3$ and/or $KHCO_3$. Preferably, the relative molar ratio of the bicarbonate salt to the creatine compound is within the range of from 1:10 to 10:1, more preferably 1:9 to 9:1, still more preferably 8:1 to 1:8, yet more preferably 7:1 to 1:7, most preferably 6:1 to 1:6, and in particular 5:1 to 1:5.

Preferably, the predefined volume of liquid that is needed in order to prepare the dialysis solution according to the invention from the solid preparation according to the invention is within the range of from 1 to 2000 L. Preferably, the liquid is purified water or, optionally contains one or more electrolytes and/or one or more non-ionic tonicity agents, and/or one or more buffers as described above.

A further aspect of the invention relates to the use of a creatine compound for the manufacture of a dialysis solution according to the invention or of a kit according to the invention or of a solid preparation according to the invention for haemodialysis or peritoneal dialysis.

A further aspect of the invention relates to a method for haemodialysis or peritoneal dialysis comprising the step of administering the dialysis solution according to the invention. In a preferred embodiment, the method according to the invention comprises the preceding step of preparing the dialysis solution from the kit according to the invention or from the solid preparation according to the invention.

Dialysis patients often still show some residual renal function and creatine compounds, due to their cell protective and anti-apoptotic effects can protect renal cells and stop or delay further degeneration and cell death in the kidney.

Further, during the dialysis process, blood cells are subjected to metabolic, mechanical, osmotic and oxidative and other stresses, which can lead to loss of cell function and cell death. Thus, in dialysis patients, creatine compounds energetically charge blood cells, protect the cell against metabolic and oxidative stress and protect its membranes against mechanical stress, thus counteracting the loss of red blood cells, and together with erythropoietin (EPO) act synergistically to prevent anemia, a problem commonly encountered in haemodialysis patients. In addition, white blood cells, that is, cells of the immune system will also be protected by creatine compounds including phospho-creatine from energy loss due to creatine depletion and by stabilizing cell membranes will protect these cells against mechanical stress. Thus, creatine compounds maintain proper cell function and strengthen the patients immune system.

Due to their anti-catabolic effects (by increased of secretion of growth hormone and muscle differentiation factors), supplementation by creatine compounds improves muscle cell mass, muscle cell function, proliferation and differentiation and finally overall muscle cell performance (force generation), parameters that are all highly relevant quality of life parameters for haemodialysis patients.

The neuro-protective effects of creatine compounds are well documented and haemodialysis patients take advantage from brain and nerve cell protection by creatine compounds, resulting in lower fatigue levels, improved memory and learning function and general well-being.

Creatine enhances bone cell proliferation, differentiation and mineralization thus counteracting, osteoporosis, osteomalacia and adynamic bone disease, problems often encountered in haemodialysis patients.

Furthermore, supplementation by creatine compounds leads to protection of body cells and tissues, against oxidative stress, lipid peroxidation, advanced glycation end products (AGE's).

Accordingly, another aspect of the invention relates to the use of a creatine compound for the manufacture of a dialysis solution according to the invention or of a kit according to the invention or of a solid preparation according to the invention for achieving any of the above advantages in the course of haemodialysis or peritoneal dialysis.

The following example further illustrates the invention but is not o be construed as limiting its scope.

EXAMPLE

As a preferred practical example for an actual clinical set-up, 0.1-30 g creatine are added to the dialysis concentrate of 4.7 liters, (normally used for one dialysis treatment per patient per day, in a Fresenius dialysis machine) to give a final concentration of 0.16-48 mM of creatine in the concentrated dialysis fluid or stock solution.

With a typical dialysis flux rate of 800 ml/min over a period of 4 hrs, amounting to a dilution of the above concentrated dialysis fluid during the dialysis process to a final volume of 192 liters of actual dialysis fluid (corresponding to a dilution factor of the dialysis stock solution of approximately 40 fold), the effective creatine concentrations in the final dialysis solution will be 0.004-1.2 mM.

Since the creatine Transporter Protein (CrT) in the plasma membrane has a very high affinity to creatine with a Km of approximately 25-30 μM, the latter concentrations of creatine in the final dialysis liquid (0.004-1.2 mM) are in the range of or significantly above the Km of the creatine transporter, such that efficient uptake of creatine by the cells from the final dialysis liquid is guaranteed.

Typically, 20-30 g of Cr added to 4.7 liters of dialysis concentrate are used to give a Cr concentration of 32 mM-48 mM stock concentration, getting diluted in the final dialysis fluid of 0.8-1.2 mM. Since the patients blood continuously sees these concentrations of creatine during the entire treatment, and since the CrT is efficient in transporting creatine into the cells, the cells have the chance of loading up with creatine.

The invention claimed is:

1. A dialysis solution for haemodialysis or peritoneal dialysis, said solution having a theoretical osmolarity within a range from 250 to 550 mosm/L and a pH value within a range from 4.9 to 8.0, said solution comprising a creatine compound and one or more electrolytes, wherein a concentration of the creatine compound is not more than 50 mM.

2. The dialysis solution according to claim 1, wherein the concentration of the creatine compound is within the range from 0.001 to 2.5 mM.

3. The dialysis solution according to claim 1, wherein the creatine compound is selected from the group consisting of creatine and physiologically acceptable salts thereof.

4. The dialysis solution according to claim 1, which further comprises:
   one or more non-ionic tonicity agents; and/or
   one or more buffers.

5. The dialysis solution according to claim 4, wherein said one or more electrolytes, said one or more non-ionic tonicity agents, and/or said one or more buffers are:
   a) 1.0 to 250 mM glucose; and/or
   b) 100 to 180 mM $Na^+$; and/or
   c) 0.5 to 5.0 mM $K^+$; and/or
   d) 0.5 to 2.0 mM $Ca^{2+}$; and/or
   e) 0.25 to 1.50 mM $Mg^{2+}$; and/or
   f) 75 to 130 mM $Cl^-$; and/or
   g) 20 to 50 mM $HCO_3^-$; and/or
   h) 20 to 50 mM lactate; and/or
   i) 2.0 to 7.5 mM acetate.

6. A kit configured for a preparation of the dialysis solution according to claim 1 comprising:
   a) a first component composition;
   b) a second component composition; and
   c) optionally, one or more further component composition(s);
   wherein the first component composition, the second component composition and the optionally one or more further component composition(s) are adapted to yield the dialysis solution according to claim 1 when being mixed with one another.

7. The kit according to claim 6, which is a multi-chamber bag system containing the first component composition, the second component composition and the optionally one or more further component composition(s) in chambers separated from one another by breakable connecting arrangement(s), where the first component composition, the second component composition and the optionally one or more further component composition(s) can be mixed, following a breaking of the breakable connecting arrangement(s), thereby yielding the dialysis solution.

8. The kit according to claim 6, wherein the first component composition is a sterilized solution containing a non-ionic tonicity agent and an acid and having a pH value below 6.0; wherein the second component composition is a sterilized solution containing a buffer and having a pH value above 7.0;

wherein the first component composition and/or the second component composition and/or the optionally one or more further component composition(s) contain one or more electrolytes; and wherein the first component composition and/or the second component composition and/or the optionally one or more further component composition(s) contain the creatine compound.

9. The kit according to claim 6, wherein the second component composition contains the total amount of the creatine compound.

10. A solid preparation adapted for the preparation of the dialysis solution according to claim 1 when being dissolved in a predefined volume of a liquid.

11. The solid preparation according to claim 10, which contains a bicarbonate salt.

12. The solid preparation according to claim 11, wherein a relative molar ratio of the bicarbonate salt to the creatine compound is within a range from 1:10 to 10:1.

13. The solid preparation according to claim 10, wherein the predefined volume of a liquid is within a range from 1 to 2000 L.

14. The solid preparation according to claim 10, wherein the liquid is purified water only or, optionally purified water containing one or more electrolytes and/or one or more non-ionic tonicity agents and/or one or more buffers.

15. The dialysis solution according to claim 1, wherein the concentration of the creatine compound is not more than 30 mM.

16. The dialysis solution according to claim 1, wherein the concentration of the creatine compound is not more than 20 mM.

17. The dialysis solution according to claim 1, wherein the concentration of the creatine compound is not more than 10 mM.

18. The dialysis solution according to claim 1, wherein the concentration of the creatine compound is not more than 5 mM.

19. The dialysis solution according to claim 5, wherein the concentration of the creatine compound is within a range from 0.004 to 1.2 mM.

20. The dialysis solution according to claim 5, wherein the concentration of the creatine compound is within a range from 0.8 to 1.2 mM.

* * * * *